United States Patent [19]
Swafford

[11] Patent Number: 5,167,646
[45] Date of Patent: Dec. 1, 1992

[54] DISPOSABLE DOUCHE MEANS WITH ADJUSTABLE NOZZLE

[76] Inventor: Ezekiel H. Swafford, Highway 72 West, Bridgeport, Ala. 35740

[21] Appl. No.: 862,447

[22] Filed: Apr. 2, 1992

[51] Int. Cl.⁵ .............................................. A61M 31/00
[52] U.S. Cl. ...................................... 604/275; 604/39; 604/279
[58] Field of Search ................ 604/27, 33, 36, 48, 604/37, 39, 40, 41, 42, 43, 257, 275, 262, 279, 277

[56] References Cited

U.S. PATENT DOCUMENTS

| | | | |
|---|---|---|---|
| 933,578 | 9/1909 | Perkins | 604/40 |
| 1,050,803 | 1/1913 | Buckner | 604/41 |
| 1,852,351 | 4/1932 | Lewis | 604/40 |
| 1,969,175 | 8/1934 | Kilgour | 604/40 |
| 2,120,367 | 6/1938 | Lewis | 604/275 |
| 3,371,665 | 3/1968 | Druckenmiller et al. | 604/275 |
| 3,426,759 | 2/1969 | Smith | 604/40 |
| 3,474,788 | 10/1969 | Corbin et al. | 604/275 |
| 3,478,743 | 11/1969 | Ericson | 604/37 |
| 4,769,015 | 9/1988 | Bloxom, Jr. | 604/27 |
| 5,009,635 | 4/1991 | Scarberry | 604/37 |

Primary Examiner—Paul J. Hirsch

[57] ABSTRACT

A disposable douche includes a inexpensive plastic container or bag sealed to one end of a small diameter plastic tube extending from a lower portion of the container. A nozzle structure is disposed on the other end of tube in a slidable manner. The nozzle structure is provided with openings in wall portions of the structure that permit liquid to flow from the structure. The nozzle structure includes further an end cone for seating in the tube end within the nozzle to prevent the flow of liquid from the nozzle.

5 Claims, 1 Drawing Sheet

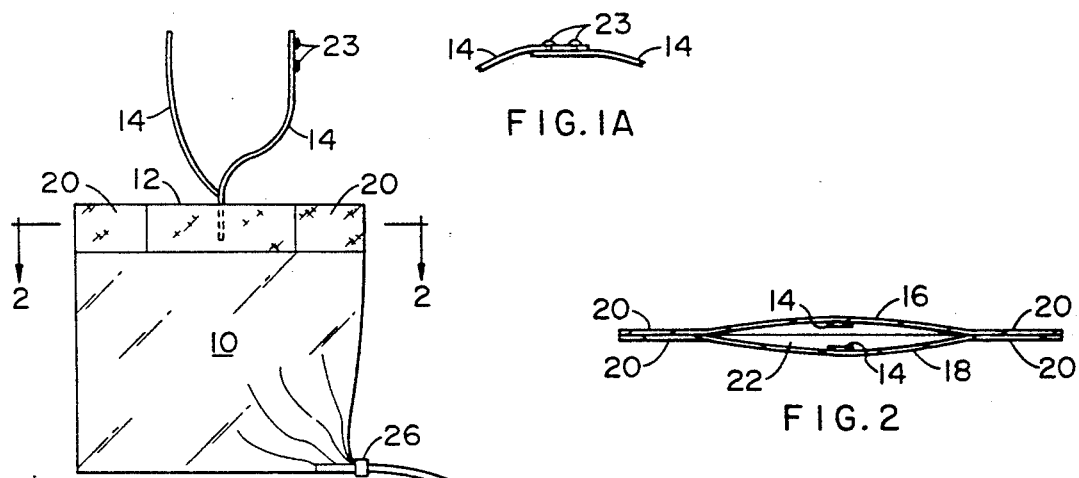
FIG. 1A
FIG. 1
FIG. 2
FIG. 5
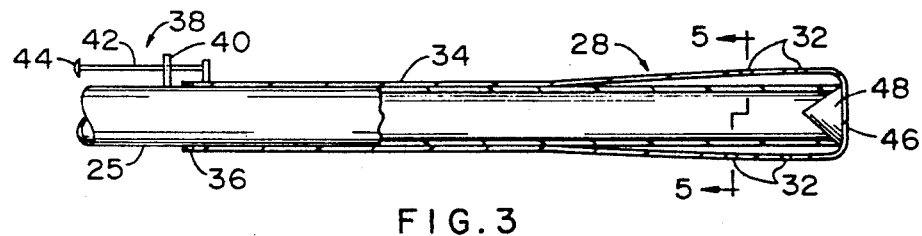
FIG. 3
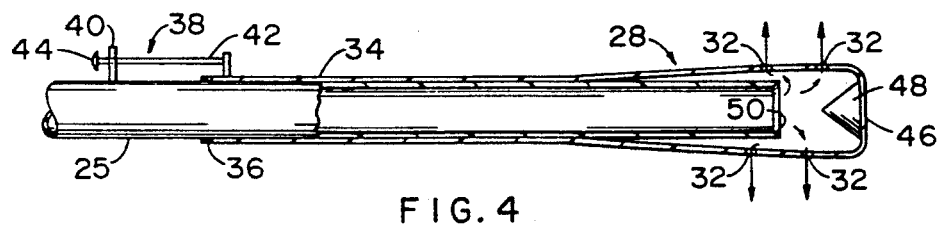
FIG. 4

DISPOSABLE DOUCHE MEANS WITH ADJUSTABLE NOZZLE

BACKGROUND ON THE INVENTION

The present invention relates generally to a portable container means of holding a small quantity of an antiseptic solution, as would be employed in a vaginal douche, in combination with a specially designed nozzle that facilitates control of liquid flow from the container by gravity through the nozzle.

Because of the need to prevent the spread of sexually transmitted bacteria and viruses, there is an ever growing need to provide inexpensive, readily available douching means and devices. The cost of any such means will affect their use, obviously, i.e., a relatively inexpensive device will be easier to purchase. For example, if a device is of negligible or minimal cost, it can be provided in substantially every room of every motel and hotel. Similarly, if it is appropriately packaged and priced, such devices can be made available in ready-to-use accessible vending machines. Such availability would be translated into widespread use so that the net result will be at least some curtailment of the spread of disease.

SUMMARY OF THE INVENTION

The present invention meets the above need by using inexpensive plastic sandwich bags, the type that are readily available in grocery stores and supermarkets, as a container for holding antiseptic solutions. The upper portion of the bag can be provided with a reinforced band of approximately one and one-half inches to provide a certain strength and integrity to the bag, particularly if it is wished to hang the bag from a supporting structure. In addition, the open end of the bag is permanently sealed near the lateral extremities so that only a limited portion of the bag can be opened for the insertion of water and a medicinal powder, for example, to be mixed in the bag. If the bag is provided with a ziplock feature it is easily reclosed to contain the liquid. A limited size opening also prevents liquid from sloshing out of the bag.

A plastic tube extends from a lower portion of the bag to a nozzle means for controlling the flow of liquid from the bag. The nozzle, like the bag, is an inexpensive device, made of a suitable plastic material, such as one that can be inexpensively injection molded. The end of the tube remote from the bag extends into the nozzle and is sealed to the nozzle by a suitable grommet or washer at the rear of the nozzle, the grommet or washer having an opening slightly less than that of the outer diameter of the tube. The tube is slidable in the nozzle, and the nozzle is provided with a rearwardly facing cone shaped protrusion that engages the end of the tube when the tube is fully inserted into the nozzle.

When the nozzle is moved relative with the tube end such that the cone is moved from the tube end, fluid flows from the tube through openings provided in the nozzle wall to the exterior of the nozzle.

Means are provided to prevent complete removal of the nozzle from the end of the tube, as discussed in detail hereinafter.

The bag, tube and nozzle can be easily packaged with a medicinal powder and thus made ready for use in public and private locations, as well as being suitable for automatic dispensing from publicly available vending machines.

THE DRAWING

The invention, along with its objectives and advantages, will best be understood from consideration of the following detailed description and the accompanying drawing in which:

FIG. 1 shows in elevation the combination of an inexpensive plastic bag, a small length of plastic tube and a inexpensive easily molded nozzle at the remote end of the tube.

FIG. 1A is a partial sectional view of the ends of a hanger strap device shown in FIG. 1, FIG. 2 is a cross section of the upper proportion of the bag of FIG. 1 taken along lines 2—2 of FIG. 1, FIG. 3 is a longitudinal section of the nozzle of FIG. 1 taken along lines 3—3 of FIG. 1, FIG. 4 is a longitudinal section of the nozzle showing it in an "open" position to permit the flow of liquid through and from the nozzle, and FIG. 5 is a cross sectional view of the nozzle of FIG. 3 taken along lines 5—5 of FIG. 3.

PREFERRED EMBODIMENTS

Referring now to FIG. 1 of the drawing, a light weight, inexpensive plastic bag 10 is shown for holding an antiseptic liquid. Preferably, the bag is provided with an upper reinforced strengthening band 12, which band may consist of an additional layer or layers of plastic material, or other suitable material. The thickness of the material of the bag can be on the order of 0.5 mils, while that of band 12 may be 1.5 mils. The reinforced band provides the capability of hanging the bag from a suitable support means (not shown) by straps 14 appropriately attached to band 12. The overall size of bag 10 can be on the order of seven inches wide and eight and one-half inches high. Such a size provides a volume capacity of about one quart of liquid.

FIG. 2 of the drawing shows opposed walls 16 and 18 of band 12 sealed together at the outer edges 20 of the bag such that a restricted center portion 22 is provided, i.e., the seals 20 restrict the size of the bag opening so that when the bag contains a liquid, the liquid will not be easily spilled from the bag. Similarly, straps 14, when connected together, such as shown in FIG. 1A, and disposed over an appropriate support item, will tend to maintain the upper portion of the bag in a closed position. The straps can be connected together by well known plastic snap hooks or buttons 22, located on one strap, that pop through appropriately sized openings provided in the other strap when the buttons are pressed into the openings.

One end of a flexible plastic tube 25 is shown extending from a lower corner of bag 10 and sealed thereto by a suitable ring means 26 that gathers the material of bag about the tube end. The tube and bag, however, can be integrally formed so that the joint effected by the ring is unnecessary.

The other end of tube 25 is located in a nozzle structure designated generally by numeral 28. The nozzle structure in cross section is shown in FIG. 5. As such, the structure includes thick side or longitudinal wall portions 30 (four being depicted in FIG. 5) and four side or longitudinal thin wall portions located between the respective thick wall portions. Openings 32 are provided in the thin wall portions to permit the flow of liquid from the nozzle, as shown in FIG. 4 of the drawing.

The inside diameter of the rear portion 34 of the nozzle structure is sized to receive an end portion of tube 25 in a manner that permits a close rubbing fit yet also permits relative sliding of the two components. To insure proper sealing of the two components so that liquid flowing through the tube will not leak from the rear of the nozzle, a small resilient ring or washer 36 is located at the rear of the nozzle structure, the ring having a slightly smaller inner diameter, say ten thousandth, than that of the outside diameter of tube 25. The ring or washer can be attached to the rearwardly facing surface of nozzle portion 34 by a suitable adhesive or it can be made as an integral part of the rear of the nozzle.

A nozzle retention means 38 is also provided at the rear of nozzle 28 in the form of a tab 40 affixed to tube 25 and receiving therethrough a small diameter rod 42 having a head 44 located on the side of tab 40 away from the nozzle. The other end of rod 42 is suitably fixed to nozzle portion 34. Head 44 abuts against tab 40, when tube 25 is withdrawn from the forward end of the nozzle, to prevent uncoupling of tube 25 and nozzle 28.

An end wall 46 of nozzle 28 is provided with an inwardly cone shaped structure 48. The pointed end of the structure faces in the direction of tube 25. The size and shape of the cone is such that it fits into the end of tube in a manner that closes and seals the tube end when the tube end is moved into place against the cone surface. The end of the tube can be provided with an inward bevel 50, as best seen in FIG. 4, to better seat on the cone surface.

The apparatus, as thus described, is used in the following manner: An antiseptic liquid is poured or mixed in, in the case of powdered ingredients, container 10. Powdered ingredients would be mixed with water. The container is then hung on a suitable object at a level at which the liquid can flow by force of gravity from the container through tube 25 to nozzle 28 when the nozzle is disposed at a level lower than the container. In FIG. 3 of the drawing, nozzle 28 is shown in a "closed" position so that no liquid can flow from the nozzle. As shown, the end of tube 25 located within the nozzle abuts against cone 48 to prevent any liquid within the tube from flowing from the tube end. The rear seal effected by washer 36 prevents leakage from the rear of the nozzle.

Nozzle 28 can now be inserted into a body cavity of a person, depending upon the specific need of the individual, and tube 25 and the nozzle relatively translated to move the tube end from cone 48. This allows the liquid in container 10 and in the tube to flow from the nozzle through openings 32 in the nozzle wall and thus into the body cavity. Openings 32, being located in the "valleys" of the nozzle structure, as best seen in FIG. 5, are not blocked by body tissue when the nozzle is disposed in the body cavity, since the thick wall portions 30 of the nozzle (see again FIG. 5) keep body tissue from pressing against the openings.

When this procedure is finished, the container, tube and nozzle can be discarded, as these components are not costly items. If they are provided by such public institutions as hotels, a plurality of the components, in a package form, can be made available. Or, as mentioned earlier, they can be inexpensively made available in vending machines. By using inexpensive sandwich bags, small diameter plastic tubing and the simple nozzle structure of the invention, which can be injection molded from low cost plastic materials, the invention provides a low cost douche means.

What is claimed is:

1. Disposable douche means, comprising:
   a lightweight disposable plastic container having an opening for receiving a liquid,
   a small elongated flexible tube extending from a portion of said container located generally opposite said opening such that when the opening is facing in an upward direction the tube extends from a lowermost portion of the container,
   a nozzle located on an end portion of the tube remote from the bag and enclosing said end portion, said nozzle being slidable on said tube end portion to open and close the same, and having end and side walls, and
   a plurality of openings provided in the side walls such that when the nozzle end wall is moved away from the tube end, one or more of the openings are exposed for the flow of liquid therethrough.

2. The means of claim 1 in which the end wall of the nozzle is provided with an inwardly directed cone structure for seating in the tube end in a manner that closes the same.

3. The means of claim 1 in which the tube and container are integrally formed to form a sealed connection therebetween.

4. The douche means of claim 1 including means to prevent the nozzle from being removed from the tube end portion located within the nozzle.

5. The means of claim 1 in which the nozzle has relatively thick and thin side wall portions, with said openings being located in the thin wall portions.

* * * * *